US00PP32136P3

(12) United States Plant Patent
van Heesbeen

(10) Patent No.: US PP32,136 P3
(45) Date of Patent: Aug. 25, 2020

(54) ***STOKESIA* PLANT NAMED 'MINI MELS'**

(50) Latin Name: *Stokesia laevis*
Varietal Denomination: Mini Mels

(71) Applicant: Van Heesbeen Cultures B.V., Rijsbergen (NL)

(72) Inventor: Ad van Heesbeen, Rijsbergen (NL)

(73) Assignee: Van Heesbeen Cultures B.V., Rijsbergen (NL)

( * ) Notice: Subject to any disclaimer, the term of this patent is extended or adjusted under 35 U.S.C. 154(b) by 0 days.

(21) Appl. No.: 16/501,668

(22) Filed: May 20, 2019

(65) Prior Publication Data

US 2019/0357413 P1 Nov. 21, 2019

(30) Foreign Application Priority Data

May 18, 2018 (QZ) ..... PBR 2018/1336

(51) Int. Cl.
*A01H 6/14* (2018.01)

(52) U.S. Cl.
USPC ..... Plt./484
CPC ..... *A01H 6/14* (2018.05)

(58) Field of Classification Search
USPC ..... Plt./484
See application file for complete search history.

(56) References Cited

U.S. PATENT DOCUMENTS

PP10,660 P * 10/1998 Warren ..... Plt./488

* cited by examiner

*Primary Examiner* — Susan McCormick Ewoldt
(74) *Attorney, Agent, or Firm* — Samuel R. McCoy, Jr.

(57) ABSTRACT

A new and distinct *Stokesia* plant named 'Mini Mels' which is characterized by the combination of a compact globular habit, small dark purple flowers with yellow centers, and the stability of these characteristics from generation to generation.

2 Drawing Sheets

Latin name of the genus and species: The Latin name of the genus and species of the novel variety disclosed herein is *Stokesia laevis*.

Variety denomination: The inventive cultivar of *Stokesia* disclosed herein has been given the variety denomination 'Mini Mels'.

CROSS REFERENCE TO RELATED APPLICATIONS

This application claims priority to the Community Plant Variety Rights application number 2018/1336, filed May 18, 2018, which is herein incorporated by reference.

BACKGROUND OF THE INVENTION

Parentage: 'Mini Mels' is a seedling selection resulting from the controlled pollination of the seed parent, *Stokesia laevis* 'Mels Blue' (U.S. Pat. No. 23,090), with an unnamed *Stokesia laevis* plant (not patented), the pollen parent. The crossing was made by the inventor in August of 2015 at a commercial greenhouse in Rijsbergen, the Netherlands. In August of 2016, one seedling from said cross was observed which exhibited smaller, dark purple flowers. The seedling was isolated for further evaluation in order to confirm the distinctness and stability of the characteristics first observed. Upon confirmation of distinctness and stability, 'Mini Mels' was selected for commercialization.

Asexual Reproduction: Asexual reproduction of 'Mini Mels', by way of softwood stem cuttings, was first performed in August of 2017 in Rijsbergen, the Netherlands.

Through five subsequent generations, the unique features of this cultivar have proven to be stable and true to type.

SUMMARY OF THE INVENTION

The cultivar 'Mini Mels' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Mini Mels'. These characteristics in combination distinguish 'Mini Mels' as a new and distinct *Stokesia laevis* cultivar:

1. *Stokesia* 'Mini Mels' exhibits a relatively compact plant size; and
2. *Stokesia* 'Mini Mels' exhibits a globular plant shape; and
3. *Stokesia* 'Mini Mels' exhibits small, dark purple flowers which are conspicuously centered yellow.

BOTANICAL DESCRIPTION OF THE PLANT

Figure 1:
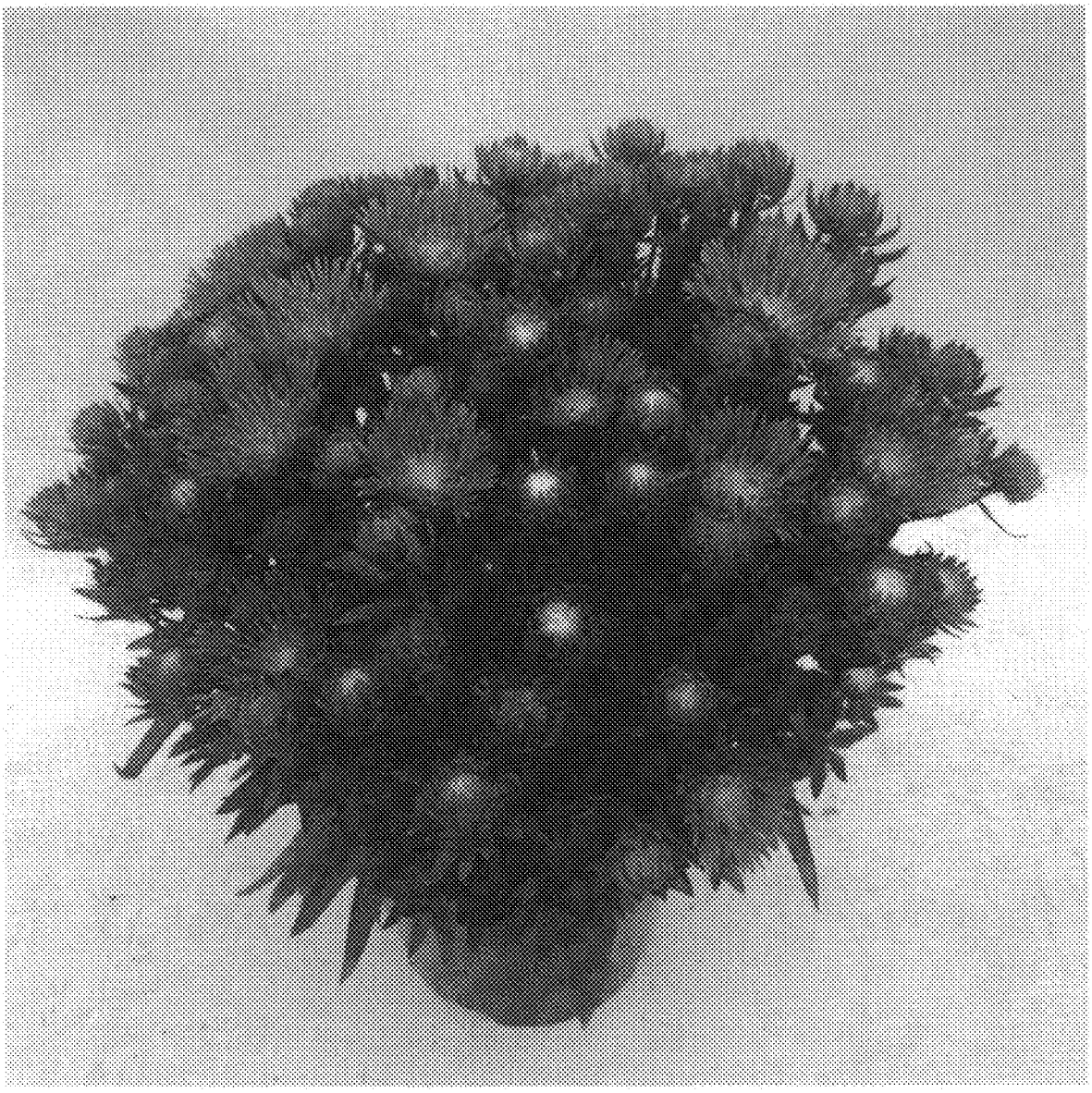
FIG. 1 illustrates, as nearly true as it is reasonably possible to make the same in color photographs of this type, an exemplary mature 'Mini Mels', at 5 months of age, plant grown outdoors at the inventor's commercial greenhouse in Rijsbergen, the Netherlands.
Figure 2:
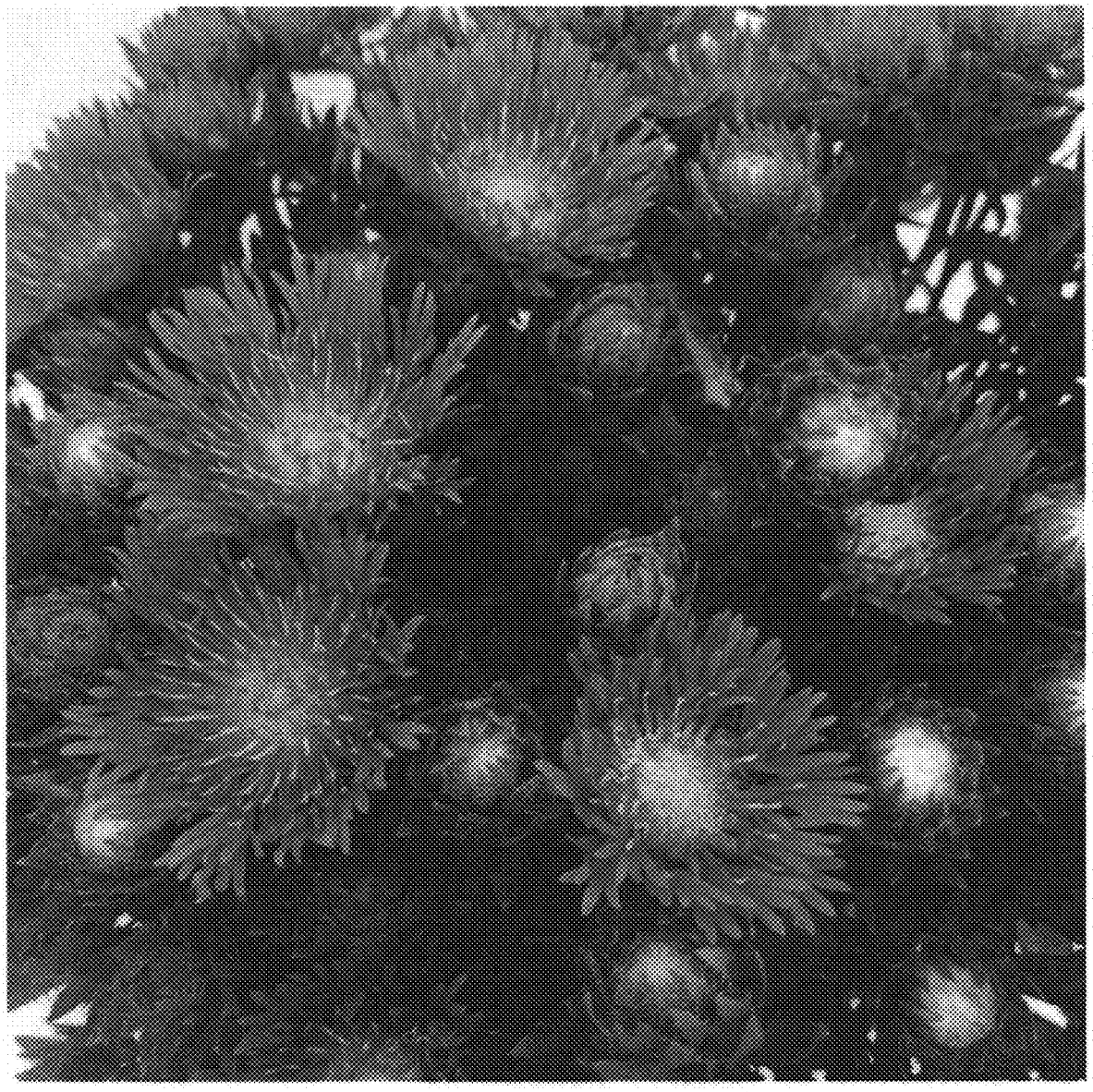
FIG. 2 illustrates, as nearly true as it is reasonably possible to make the same in color photographs of this type, the typical flowers of 'Mini Mels'.

The following observations and measurements, made in September of 2019, describe averages from a sample set of six specimens of one year old 'Mini Mels' plants grown in 17 cm nursery containers in Rijsbergen, the Netherlands. Plants were produced outdoors with full sun exposure and maintained using overhead irrigation at regular intervals, and were fertilized as required using a slow release fertilizer. No chemical pest control measures were utilized during production.

Those skilled in the art will appreciate that certain characteristics will vary with older or, conversely, with younger plants. 'Mini Mels' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 edition.

A botanical description of 'Mini Mels' and comparisons with the parents and most similar variety of common knowledge are provided below.

General plant description:

*Growth habit*.—A broad, upright herbaceous perennial with inflorescence carried within and above the foliage.

*Plant profile*.—Obovate.

*Height*.—30.5 cm to the top of the foliar plane; 34.4 cm to the top of the floral plane.

*Spread*.—30.0 cm.

*Plant vigor*.—Moderately vigorous.

*Growth rate*.—Moderately fast growing.

*Propagation*.—Method — Softwood stem cuttings. Time to initiate rooting — Rooting is initiated in approximately 14 days when grown in a greenhouse with an ambient average temperature of 15 degrees Celsius. Time to produce a finished plant — Approximately 12 weeks are required to produce a marketable finished plant in an 11 cm pot.

*Pest resistance and susceptibility*.—Not any more or less tolerant or susceptible to pests or diseases known to effect *Stokesia*.

*Environmental tolerances*.—Cold hardy to USDA Hardiness Zone 6 and temperatures as high as 35 degrees Celsius; drought tolerant once established.

Root system:

*General*.—Moderately freely branched and moderately dense rooting.

*Distribution in the soil profile*.—Shallow to moderately deep.

*Texture*.—Non-fibrous, non-fleshy.

*Color*.—Yellow-white, nearest to a mixture of RHS 158C and 158D.

Stem:

*Branching habit*.—Basally branching main stem; freely branching with lateral branches.

*Number of main stems per plant*.—30.

*Number of lateral branches per main stem*.—2.

*Aspect of main stems and lateral branches*.—Rounded.

*Lateral branch length*.—15.1 cm.

*Lateral branch diameter*.—0.4 cm.

*Internode length*.—4.3 cm.

*Attitude*.—Main stems are an average angle of 15 degrees from vertical; stems vary from between 0 to 35 degrees from vertical. Lateral branches are at an average angle of 20 degrees to the main stems.

*Strength*.—Moderately strong.

*Pubescence*.—Densely covered with short, sericeous hairs with an average length of 0.15 cm and colored greyed-white, nearest to RHS 156D.

*Luster*.—Matte.

*Color, juvenile*.—Yellow-green, nearest RHS 146D.

*Color, mature*.—Yellow-green, nearest to in between RHS 144B and 146D, and occasionally suffused with greyed-orange, nearest to RHS 177A.

*Color at internodes*.—Yellow-green, nearest to in between RHS 144B and 146D.

Foliage:

*General*.—Leaves are borne both basally and on stems.

*Basal leaves*.—Arrangement — Alternate. Attachment — Petiolate. Division — Simple. Shape — Lanceolate. Dimensions — 8.0 cm long, including petiole, and 2.1 cm wide. Attitude — Outward and upward. Apex — Acute. Base — Long acuminate. Margins — Entire; very slightly undulate. Texture and luster, adaxial and abaxial surfaces — Smooth, glabrous, and matte. Luster, adaxial and abaxial surfaces — Very slightly glossy. Color Juvenile foliage color, adaxial surface — Green, nearest to RHS 143A. Juvenile foliage color, abaxial surface — Yellow-green, RHS 146B. Mature leaf color, adaxial surface — Green, nearest to RHS 137B. Mature leaf color, abaxial surface — Nearest to in between green, RHS 138B, and yellow-green, RHS 147B. Venation — Type — Pinnate. Vein color, adaxial surface — Yellow-green, nearest to RHS 144C. Vein color, abaxial surface — Yellow-green, nearest to RHS 146D. Petiole — Length — 6.6 cm. Diameter — 0.2 cm. Strength — Medium. Texture and luster, adaxial and abaxial surfaces — Smooth, glabrous, and moderately glossy. Color, adaxial surface — Yellow-green, nearest to RHS 144C, and suffused with greyed-purple at the base, nearest to RHS 187D. Color, abaxial surface — Yellow-green, RHS 145A, and fading lighter towards the base, nearest to a mixture of RHS 150C and 150D; suffused with greyed-purple at the base, nearest to RHS 187D. Stipules — None present.

*Cauline leaves*.—Quantity — Approximately 6 leaves per stem. Arrangement — Alternate. Attachment — Sessile. Division — Simple. Shape — Lanceolate. Dimensions — 7.8 cm long, including petiole, and 2.1 cm wide. Attitude — Outward and somewhat upward. Apex — Acute. Base — Long acuminate; decurrent. Margins — Proximally serrate and becoming entire, distally; very slightly undulate. Texture and luster, adaxial and abaxial surfaces — Smooth, glabrous, and matte. Luster, adaxial and abaxial surfaces — Very slightly glossy. Color Juvenile foliage color, adaxial surface — Green, nearest to RHS 143A. Juvenile foliage color, abaxial surface — Yellow-green, RHS 146B. Mature leaf color, adaxial surface — Green, nearest to RHS 137B. Mature leaf color, abaxial surface — Nearest to in between green, RHS 138B, and yellow-green, RHS 147B. Venation — Type — Pinnate. Vein color, adaxial surface — Yellow-green, nearest to RHS 144C. Vein color, abaxial surface — Yellow-green, nearest to RHS 146D. Stipules — None present.

Inflorescence:

*Type*.—Terminal capitula comprised of a receptacle, disc florets, and ray florets.

*Natural flowering season*.—Summer into autumn in Rijsbergen, the Netherlands.

*Flowering habit*.—Very freely flowering.

*Dimensions*.—3.0 cm high, not including peduncle, and 5.1 cm in diameter.

*Quantity of inflorescence per plant*.—150, on average; typically 5 per lateral branch.

*Attitude*.—Upright.

*Peduncles*.—Length — Primary peduncles are 3.1 cm long on average; lateral peduncles are 1.6 cm on average. Diameter — Primary peduncles are 0.2 cm in diameter, on average; lateral peduncles are 0.175 cm on average. Attitude — Primary peduncles are upright; lateral peduncles are at an angle of 30 degrees to the primary peduncles. Strength — Strong. Texture — Densely pubescent; short, sericeous hairs with an average length of 0.175 cm and colored green-white, RHS 157D. Luster — Matte. Color — Yellow-green, nearest to RHS 146D.

Flower buds:

*Shape*.—Spherical.

*Length*.—Average of 1.8 cm.

*Diameter*.—Average of 1.1 cm.

*Texture*.—Smooth; glabrous.

*Luster*.—Matte.

*Color*.—Nearest to in between white and yellow-white, RHS 155A and 158D, and suffused with purple, RHS 76A.

Flower:

*Flower type*.—Composite; capitula.

*Fragrance*.—None.

*Flower longevity*.—10 days, on average.

*Persistence*.—Persistent.

*Disc diameter*.—3.5 cm.

*Receptacle shape*.—Flattened.

*Receptacle height*.—0.3 cm.

*Receptacle diameter*.—0.6 cm.

*Receptacle color*.—Green-white, nearest to RHS 157A.

*Ray florets*.—Quantity of florets per capitula — 11. Shape — Flabellate; proximal 40 percent of the floret is tubular. Arrangement — Rotate with a single whorl of florets around disc; florets are unfused. Attitude — Outward, with an average angle of 25 degrees to horizontal. Aspect — Carinate. Dimensions — 2.5 cm long and 1.5 cm wide. Apex — Lanciniate with 5 or 6 acute lobes. Base — Long, narrow cuneate. Margin — Entire; not undulated. Texture and luster, upper surface — Glabrous, moderately velvety and slightly glossy. Texture and luster, lower surface — Glabrous, moderately velvety and moderately glossy. Color, when opening, upper surface — Violet, nearest to 86B, and fading to white towards the base, nearest to RHS N155A. Color, when opening, lower surface — Violet, nearest to in between RHS 86B and 86C, and fading to white towards the base, nearest to RHS N155A. Color, when fully opened, upper surface — Violet, nearest to 86B, and fading to white towards the base, nearest to RHS N155A. Color, when fully opened, lower surface — Violet, nearest to in between RHS 86B and 86C, and fading to white towards the base, nearest to RHS N155A. Venation, when fully opened, upper surface — No visible venation. Venation, when fully opened, lower surface — No visible venation. Faded color, upper surface — Violet, nearest to RHS N87A, and fading lighter towards the base, nearest to RHS 85A. Faded color, lower surface — Violet, nearest to RHS N87A, and fading lighter towards the base, nearest to RHS 85A.

*Disc florets*.—Quantity of florets per capitula — 140. Arrangement — Radial symmetry; five whorls of florets. Shape — Tubular; proximal 50 percent of florets are fused, typically with 5 free apical lobes. Attitude — Upright and outward; at an average angle of 20 degrees to horizontal. Length — 1.7 cm. Width — 0.6 cm. Apex of the floret lobe — Lanciniate; apical lobes are narrowly acute. Base — Fused into a tube. Margin of the free floret lobe — Entire; not undulated. Texture and luster, upper surface — Smooth, glabrous and very slightly glossy. Texture and luster, lower surface — Smooth, glabrous and moderately glossy. Color, when opening, upper surface — Violet, nearest to RHS 86B, and fading to white towards the base, nearest to RHS N155A. Color, when opening, lower surface — Violet, nearest to RHS 86C, and fading to white towards the base, nearest to RHS N155A. Color, when fully opened, upper surface — Violet, nearest to RHS 86B, and fading to white towards the base, nearest to RHS N155A. Color, when fully opened, lower surface — Violet, nearest to RHS 86C, and fading to white towards the base, nearest to RHS N155A. Faded color, upper surface — Not fading. Faded color, lower surface — Not fading. Venation, upper and lower surfaces — No visible venation. Disc floret bracts — Quantity — One bract is present at the base of each disc floret. Arrangement — Rotate. Length — 0.8 cm. Diameter — 0.5 cm. Shape — Linear. Apex — Narrowly acute. Base — Cuneate. Margin — Entire. Texture and luster — Smooth, glabrous, and glossy. Color — White, nearest to RHS NN155A.

*Involucre; phyllaries*.—Arrangement — Rotate; free; five whorls around the disc with the upper whorl exhibiting unique morphological characteristics relative to the lower four whorls. Quantity — 40. Upper whorl of phyllaries — Length — 0.7 cm. Width — 0.3 cm. Shape — Elliptic. Apex — Acute. Base — Cuneate. Margin — Lacerate. Texture and luster, upper surface — Glabrous; very slightly glossy. Texture and luster, lower surface — Glabrous; matte. Color, fully opened, upper surface — Green, nearest to RHS 143B. Color, fully opened, lower surface — Green, nearest to RHS 143A. Lower whorls of phyllaries — Length — 1.4 cm. Width — 0.7 cm. Shape — Ovate to elliptic. Apex — Acute. Base — Cuneate. Margin — Lacerate. Texture and luster, upper surface — Glabrous; very slightly glossy. Texture and luster, lower surface — Glabrous; matte. Color, fully opened, upper surface — Green, nearest to RHS 143B. Color, fully opened, lower surface — Green, nearest to RHS 143A.

Reproductive organs:

*Androecium*.—Stamens — Quantity — 5 per disc floret; none present on ray florets. Anthers — Shape — Narrow oblong. Dimensions — Approximately 0.2 cm long and 0.05 cm wide. Color — White, nearest to RHS 155A. Filaments — Length — 1.0 cm. Color — Purple, nearest to RHS 85C. Pollen, amount — Moderately abundant. Pollen color — White, nearest to RHS NN155D.

*Gynoecium*.—Pistil — Quantity — 1 pistil for each disc floret; no pistils present on ray florets. Length — 1.6 cm. Style — Length — 1.4 cm. Color — Purple, nearest to in between RHS 85C and 85D. Stigma — Shape — Cleft; decurrent. Diameter — 0.3 cm. Color — Purple, nearest to RHS 85D. Ovary Color — White, nearest to RHS 155C.

Seed and fruit: Botanical description is not yet available.

COMPARISONS WITH THE PARENTS

Plants of the new cultivar 'Mini Mels' differ from its parent, *Stokesia laevis* 'Mels Blue' (U.S. Pat. No. 23,090), by the characteristics described in Table 1.

TABLE 1

| Characteristic | 'Mini Mels' | 'Mels Blue' |
|---|---|---|
| Plant height. | Shorter than 'Mels Blue'. | Taller than 'Mini Mels'. |
| General coloration of the flower. | Dark purple and centered yellow. | Violet to violet-blue and centered white. |

Plants of the new cultivar 'Mini Mels' differ from its pollen parent, an unnamed *Stokesia laevis* plant (not patented), by the characteristics described in Table 2.

TABLE 2

| Characteristic | 'Mini Mels' | The pollen parent |
|---|---|---|
| Abundance of foliage. | More abundant. | Less abundant. |
| Foliage thickness. | Thicker than the pollen parent. | Thinner than 'Mini Mels'. |

TABLE 2-continued

| Characteristic | 'Mini Mels' | The pollen parent |
|---|---|---|
| General coloration of mature foliage. | Darker green. | Lighter green. |
| Floriferousness. | More flowers per plant. | Fewer flowers per plant. |
| General coloration of the flower. | Darker purple. | Lighter purple. |

COMPARISONS WITH THE MOST SIMILAR VARIETY OF COMMON KNOWLEDGE

Plants of the new cultivar 'Mini Mels' may be distinguished from the variety *Stokesia laevis* 'Mega Mels' (U.S. patent application Ser. No. 16/501,670) by the combination of characteristics described in Table 3.

TABLE 3

| Characteristic | 'Mini Mels' | 'Mega Mels' |
|---|---|---|
| Flower size. | Smaller than 'Mega Mels'. | Larger than 'Mini Mels'. |
| Abundance of involucral bracts. | More abundant. | Less abundant. |
| Attitude of involucral bracts. | More upright. | More relaxed. |
| General coloration of the flower. | Dark purple; conspicuously centered with a lighter shade of yellow, | Light purple; inconspicuously centered with a darker shade of yellow. |

That which is claimed:

1. A new and distinct cultivar of *Stokesia* plant named 'Mini Mels', substantially as described and illustrated herein.

* * * * *